United States Patent
Igarashi

(10) Patent No.: US 6,696,178 B2
(45) Date of Patent: Feb. 24, 2004

(54) CYCLOCONDENSED POLYCYCLIC HYDROCARBON COMPOUND AND LIGHT-EMITTING DEVICE USING THE SAME

(75) Inventor: Tatsuya Igarashi, Kanagawa (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 09/755,080

(22) Filed: Jan. 8, 2001

(65) Prior Publication Data

US 2001/0008711 A1 Jul. 19, 2001

(30) Foreign Application Priority Data

Jan. 12, 2000 (JP) ..................... P. 2000-003687

(51) Int. Cl.$^7$ ................. H05B 33/12; C07C 211/54
(52) U.S. Cl. ............... 428/690; 428/917; 313/504; 313/506; 564/308; 564/426; 564/427
(58) Field of Search ............... 428/690, 917; 313/504, 506; 252/301.16; 564/308, 309, 426, 427

(56) References Cited

U.S. PATENT DOCUMENTS 5,153,073 A * 10/1992 Ohnuma et al. ............ 428/461
5,378,519 A * 1/1995 Kikuchi et al. ............. 428/690
5,759,444 A * 6/1998 Enokida et al. ........ 252/301.16

2002/0094452 A1 * 7/2002 Ueda et al. ................. 428/690

FOREIGN PATENT DOCUMENTS

EP 0 805 143 A1 * 11/1997
EP 0 847 228 A2 * 6/1998
EP 0 965 629 A1 * 12/1999
EP 1 013 740 A2 * 6/2000

OTHER PUBLICATIONS

C.W. Tang et al., "Organic Electroluminescent Diodes," Applied Physics Letters, 51 (12), pp. 913–915 (Sep. 1987).

* cited by examiner

Primary Examiner—Marie Yamnitzky
(74) Attorney, Agent, or Firm—Sughrue Mion, PLLC

(57) ABSTRACT

An organic light-emitting device comprising a light-emitting layer or a plurality of organic compound thin layers including a light-emitting layer formed between a pair of electrodes, wherein at least one layer comprises at least one kind of compound represented by the following formula (1):

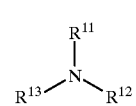

(1)

wherein $R^{11}$, $R^{12}$ and $R^{13}$ each represents a group having a cyclocondensed polycyclic hydrocarbon structure in which three or more rings are cyclocondensed; and a novel cyclocondensed polycyclic hydrocarbon compound.

14 Claims, No Drawings

CYCLOCONDENSED POLYCYCLIC HYDROCARBON COMPOUND AND LIGHT-EMITTING DEVICE USING THE SAME

FIELD OF THE INVENTION

The present invention relates to cyclocondensed polycyclic hydrocarbon compounds, light-emitting device materials which can convert electric energy to light to emit the light, and light-emitting devices. More particularly, the invention relates to light-emitting devices which can be suitably used in the fields of display devices, displays, backlights, electrophotography, illumination light sources, recording light sources, exposure light sources, reading light sources, markings, billboards, interior decorations and the like.

BACKGROUND OF THE INVENTION

At the present time, the research and development of various display devices have been actively made. In particular, organic light-emitting devices have attracted attention as promising display devices, because they can provide highly bright luminescence at low voltage. For example, a light-emitting device in which an organic thin film is formed by vapor deposition of an organic compound (*Applied Physics Letters*, 51, 913 (1987)) has been known. The light-emitting device described in this literature is substantially improved in luminescence properties compared with conventional single-layer devices, by using tris (8-hydroxyquinolinato)aluminum complex (Alq) as an electron-transporting material and laminating a hole-transporting material (amine compound) therewith.

In recent years, the application of organic light-emitting devices to full color displays has been actively studied. However, for developing high performance full color displays, it is necessary to improve properties of each of blue, green and red light-emitting devices. For example, in regard to the blue light-emitting device, distyrylarylene compounds (DPVBi) described in "The Front Line of Organic EL Devices and Their Industrialization", page 38 (supervised by Seizo Miyata, NTS Co. Ltd., 1998) have been widely studied. However, problems have arisen in terms of color purity, durability, luminescence luminance and efficiency, so that it has been desired that these problems should be solved.

Organic light-emitting devices realizing highly bright luminance are devices in which organic materials are applied by vapor deposition to form a laminate. The fabrication of the devices by coating is preferred from the viewpoints of simplification of manufacturing processes, processability and enlargement of their area. However, the devices fabricated by the conventional coating system, in particular, blue light-emitting devices are inferior in luminescence luminance and light-emission efficiency to the devices fabricated by vapor deposition. Accordingly, development of novel blue light-emitting device materials has been desired.

SUMMARY OF THE INVENITON

It is therefore an object of the invention is to provide light-emitting devices good in luminescence properties.

Another object of the invention is to provide light-emitting device materials good in luminescence properties.

The objects of the invention have been attained by the following:

(1) An organic light-emitting device comprising a light-emitting layer or a plurality of organic compound thin layers including a light-emitting layer formed between a pair of electrodes, wherein at least one layer comprises at least one kind of compound represented by the following formula (1):

(1)

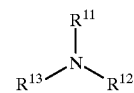

wherein $R^{11}$, $R^{12}$ and $R^{13}$ each represents a group having a cyclocondensed polycyclic hydrocarbon structure in which three or more rings are cyclocondensed;

(2) The organic light-emitting device described in the above (1), wherein the compound represented by the formula (1) is a compound represented by the following formula (2):

(2)

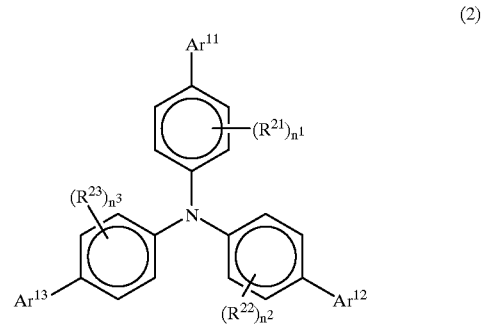

wherein $Ar^{11}$, $Ar^{12}$ and $Ar^{13}$ each represents a group having an anthracene structure, a phenanthrene structure or a pyrene structure, $R^{21}$, $R^{22}$ and $R^{23}$ each represents a substituent, and $n^1$, $n^2$ and $n^3$ each represents an integer of from 0 to 4;

(3) The organic light-emitting device described in the above (2), wherein $Ar^{11}$, $Ar^{12}$ and $Ar^{13}$ each represents an anthryl group, a phenanthryl group, a pyrenyl group, an anthrylphenyl group, a perylenyl group, a chrysenyl group, a triphenylenyl group or groups in which cyclocondensation is further conducted to these structures;

(4) The organic light-emitting device described in the above (2), wherein $Ar^{11}$, $Ar^{12}$ and $Ar^{13}$ each represents an anthryl group, an anthrylphenyl group, a phenanthryl group or a pyrenyl group;

(5) The organic light-emitting device described in the above (1), wherein the compound represented by the formula (1) is utilized as charge-transporting materials;

(6) The organic light-emitting device described in the above (1), wherein the layer comprising the compound represented by the formula (1) is formed by a coating method;

(7) A compound represented by the formula (2) described in the above (2);

(8) The compound described in the above (7), wherein $Ar^{11}$, $Ar^{12}$ and $Ar^{13}$ each represents an anthryl group, a phenanthryl group, a pyrenyl group, an anthrylphenyl group, a perylenyl group, a chrysenyl group, a triphenylenyl group or groups in which cyclocondensation is further conducted to these structures; and (9) The compound described in the above (7), wherein $Ar^{11}$, $Ar^{12}$ and $Ar^{13}$ each represents an anthryl group, an anthrylphenyl group, a phenanthryl group or a pyrenyl group.

DETAILED DESCRIPTION OF THE INVENTION

The invention will be described in detail below.

In formula (1), $R^{11}$, $R^{12}$ and $R^{13}$ each represents a group having a cyclocondensed polycyclic hydrocarbon structure in which three or more rings are cyclocondensed. The cyclocondensed polycyclic hydrocarbon structures in which three or more rings are cyclocondensed include structures described in Aldrich Structure Index, for example, pages 177 and 178, the 1996 and 1997 editions, Aldrich Co., *Library of Rare Chemicals Structure Index*, for example, pages 165 to 168, the 1993 edition, Sigma-Aldrich Co., and *Organic Chemistry-Biochemistry Nomenclature*, the first volume, pages 21 to 28, translated by Kazuo Hirayama, Nankodo (1988). Examples of the structures include an anthracene structure, a phenanthrene structure, a pyrene structure, a triphenylene structure, a perylene structure, a fluoranthene structure, an indacene structure, an acenaphthylene structure, a fluorene structure, a tetraphenylene structure and structures in which cyclocondensation is further conducted to these structures (for example, a benzanthracene structure, a benzpyrene structure, a pentacene structure, a coronene structure and a chrysene structure).

The cyclocondensed polycyclic hydrocarbon structures in which three or more rings are cyclocondensed are preferably aromatic cyclocondensed hydrocarbon structures in which three or more rings are cyclocondensed, and more preferably an anthracene structure, a phenanthrene structure and a pyrene structure.

$R^{11}$, $R^{12}$ and $R^{13}$ each has preferably from 14 to 50 carbon atoms, more preferably from 14 to 30 carbon atoms, and still more preferably from 14 to 20 carbon atoms. $R^{11}$, $R^{12}$ and $R^{13}$ are preferably groups composed of only carbon and hydrogen atoms, and more preferably groups composed of only aromatic hydrocarbon structures. $R^{11}$, $R^{12}$ and $R^{13}$ are each preferably a substituted or unsubstituted anthryl group, a substituted or unsubstituted pyrenyl group, a substituted or unsubstituted phenanthryl group, a substituted or unsubstituted anthrylphenyl group, a substituted or unsubstituted pyrenylphenyl group or a substituted or unsubstituted phenanthrylphenyl group, and more preferably a substituted or unsubstituted anthrylphenyl group, a substituted or unsubstituted pyrenylphenyl group or a substituted or unsubstituted phenanthrylphenyl group. A substituent for $R^{11}$, $R^{12}$ or $R^{13}$ includes, for example, an $R^{21}$ group described later, and is preferably an alkyl group. The term "anthryl" has the same significance as "anthracenyl" and the term "phenanthryl" has the same significance as "phenanthrenyl".

The compounds represented by formula (1) are preferably compounds represented by formula (3). Formula (3) will be described below.

(3)

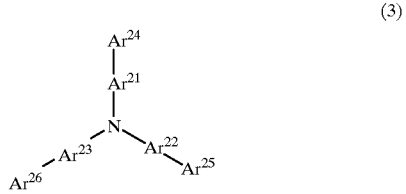

wherein $Ar^{21}$, $Ar^{22}$ and $Ar^{23}$ each represents an arylene group or a heteroarylene group, and $Ar^{24}$, $Ar^{25}$ and $Ar^{26}$ each represents an aryl group or a heteroaryl group. However, either of $Ar^{21}$ and $Ar^{24}$ is a cyclocondensed polycyclic hydrocarbon structure in which three or more rings are cyclocondensed (preferably an aromatic cyclocondensed hydrocarbon structure in which three or more rings are cyclocondensed), either of $Ar^{22}$ and $Ar^{25}$ is a cyclocondensed polycyclic hydrocarbon structure in which three or more rings are cyclocondensed (preferably an aromatic cyclocondensed hydrocarbon structure in which three or more rings are cyclocondensed), and either of $Ar^{23}$ and $Ar^{26}$ is a cyclocondensed polycyclic hydrocarbon structure in which three or more rings are cyclocondensed (preferably an aromatic cyclocondensed hydrocarbon structure in which three or more rings are cyclocondensed).

$Ar^{21}$, $Ar^{22}$ and $Ar^{23}$ each has preferably from 6 to 30 carbon atoms, more preferably from 6 to 20 carbon atoms, and still more preferably from 6 to 16 carbon atoms. The arylene groups and heteroarylene groups constituting $Ar^{21}$, $Ar^{22}$ or $Ar^{23}$ include, for example, phenylene, naphthylene, anthrylene, phenanthrylene, pyrenylene, perylenylene, fluorenylene, biphenylene, terphenylene, rubrenylene, chrysenylene, triphenylenylene, benzanthrylene, benzophenanthrylene, diphenylanthrylene, pyridylene, pyrazilene, quinolylene, quinoxalylene, quinazolylene, acridylene, phenanthridylene, phthaladylene and phenanthrolylene groups. These arylene and heteroarylene groups may further have substituents. Examples of the substituents include $R^{21}$ groups described later.

$Ar^{21}$, $Ar^{22}$ and $Ar^{23}$ are each preferably an arylene group, more preferably a phenylene group, a naphthylene group, an anthrylene group, a phenanthrylene group, a pyrenylene group, a perylenylene group or a biphenylene group, still more preferably a phenylene group, a naphthylene group, an anthrylene group, a pyrenylene group or a phenanthrylene group, and particularly preferably a phenylene group.

$Ar^{24}$, $Ar^{25}$ and $Ar^{26}$ each has preferably from 6 to 30 carbon atoms, more preferably from 6 to 20 carbon atoms, and still more preferably from 6 to 16 carbon atoms. The aryl groups and heteroaryl groups constituting $Ar^{24}$, $Ar^{25}$ or $Ar^{26}$ include, for example, phenyl, naphthyl, anthryl, phenanthryl, pyrenyl, anthrylphenyl, perylenyl, fluorenyl, biphenyl, terphenyl, rubrenyl, chrysenyl, triphenylenyl, benzanthryl, benzophenanthryl, diphenylanthryl, quinolyl, quinoxalyl, quinazolyl, acridyl, phenanthridyl, phthaladyl and phenanthrolyl groups, and groups in which cyclocondensation is further conducted to these groups. These groups may further have substituents. Examples of the substituents include $R^{21}$ groups described later, or the like.

$Ar^{24}$, $Ar^{25}$ and $Ar^{26}$ are each preferably an aryl group, more preferably a phenyl group, a naphthyl group, an anthryl group, a phenanthryl group, a pyrenyl group, an anthrylphenyl group, a perylenyl group or a biphenyl group, and still more preferably an anthryl group, a pyrenyl group, a phenanthryl group or an anthrylphenyl group, and particularly preferably a pyrenyl group or an anthrylphenyl group.

The compounds represented by formula (1) are more preferably compounds represented by formula (2). Formula (2) will be described below.

(2)

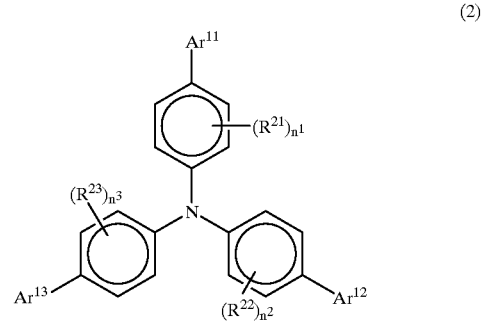

$Ar^{11}$, $Ar^{12}$ and $Ar^{13}$ each represents a group having an anthracene structure, a phenanthrene structure or a pyrene structure. Examples of $Ar^{11}$, $Ar^{12}$ and $Ar^{13}$ include an anthryl group, a phenanthryl group, a pyrenyl group, an anthrylphenyl group, a perylenyl group, a chrysenyl group, a triphenylenyl group and groups in which cyclocondensation is further conducted to these structures (for example, a benzanthryl group and a benzpyrenyl group) These groups may further have substituents.

$Ar^{11}$, $Ar^{12}$ and $Ar^{13}$ are each preferably a substituted or unsubstituted anthrylphenyl group, a substituted or unsubstituted anthryl group, a substituted or unsubstituted phenanthryl group or a substituted or unsubstituted pyrenyl group, more preferably an alkyl-substituted or unsubstituted anthrylphenyl group, an alkyl-substituted or unsubstituted phenanthryl group or an alkyl-substituted or unsubstituted pyrenyl group, and particularly preferably a pyrenyl group or a phenanthryl group. A substituent for $Ar^{11}$, $Ar^{12}$ or $Ar^{13}$ includes, for example, an $R^{21}$ group described later.

$R^{21}$, $R^{22}$ and $R^{23}$ each represents a substituent. The substituents include an alkyl group (having preferably from 1 to 30 carbon atoms, more preferably from 1 to 20 carbon atoms, and particularly preferably from 1 to 10 carbon atoms, such as methyl, ethyl, iso-propyl, tert-butyl, n-octyl, n-decyl, n-hexadecyl, cyclopropyl, cyclopentyl or cyclohexyl), an alkenyl group (having preferably from 2 to 30 carbon atoms, more preferably from 2 to 20 carbon atoms, and particularly preferably from 2 to 10 carbon atoms, such as vinyl, allyl, 2-butenyl or 3-pentenyl), an alkynyl group (having preferably from 2 to 30 carbon atoms, more preferably from 2 to 20 carbon atoms, and particularly preferably from 2 to 10 carbon atoms, such as propargyl or 3-pentynyl), an aryl group (having preferably from 6 to 30 carbon atoms, more preferably from 6 to 20 carbon atoms, and particularly preferably from 6 to 12 carbon atoms, such as phenyl, p-methylphenyl, naphthyl or anthryl), an amino group (having preferably from 0 to 30 carbon atoms, more preferably from 0 to 20 carbon atoms, and particularly preferably from 0 to 10 carbon atoms, such as amino, methylamino, dimethylamino, diethylamino, dibenzylamino, diphenylamino or ditolylamino), an alkoxyl group (having preferably from 1 to 30 carbon atoms, more preferably from 1 to 20 carbon atoms, and particularly preferably from 1 to 10 carbon atoms, such as methoxy, ethoxy, butoxy or 2-ethylhexyloxy), an aryloxy group (having preferably from 6 to 30 carbon atoms, more preferably from 6 to 20 carbon atoms, and particularly preferably from 6 to 12 carbon atoms, such as phenyloxy, 1-naphthyloxy or 2-naphthyloxy), a heteroaryloxy group (having preferably from 1 to 30 carbon atoms, more preferably from 1 t 20 carbon atoms, and particularly preferably from 1 to 12 carbon atoms, such as pyridyloxy, pyrazyloxy, pyrimidyloxy or quinolyloxy), an acyl group (having preferably from 1 to 30 carbon atoms, more preferably from 1 to 20 carbon atoms, and particularly preferably from 1 to 12 carbon atoms, such as acetyl, benzoyl, formyl or pivaloyl), an alkoxycarbonyl group (having preferably from 2 to 30 carbon atoms, more preferably from 2 to 20 carbon atoms, and particularly preferably from 2 to 12 carbon atoms, such as methoxycarbonyl or ethoxycarbonyl), an aryloxycarbonyl group (having preferably from 7 to 30 carbon atoms, more preferably from 7 to 20 carbon atoms, and particularly preferably from 7 to 12 carbon atoms, such as phenyloxycarbonyl), an acyloxy group (having preferably from 2 to 30 carbon atoms, more preferably from 2 to 20 carbon atoms, and particularly preferably from 2 to 10 carbon atoms, such as acetoxy or benzoyloxy), an acylamino group (having preferably from 2 to 30 carbon atoms, more preferably from 2 to 20 carbon atoms, and particularly preferably from 2 to 10 carbon atoms, such as acetylamio or benzoylamino), an alkoxycarbonylamino group (having preferably from 2 to 30 carbon atoms, more preferably from 2 to 20 carbon atoms, and particularly preferably from 2 to 12 carbon atoms, such as methoxycarbonylamino), an aryloxycarbonylamino group (having preferably from 7 to 30 carbon atoms, more preferably from 7 to 20 carbon atoms, and particularly preferably from 7 to 12 carbon atoms, such as phenyloxycarbonylamino), a sulfonylamino group (having preferably from 1 to 30 carbon atoms, more preferably from 1 to 20 carbon atoms, and particularly preferably from 1 to 12 carbon atoms, such as methanesulfonylamino or benzenesulfonylamino), a sulfamoyl group (having preferably from 0 to 30 carbon atoms, more preferably from 0 to 20 carbon atoms, and particularly preferably from 0 to 12 carbon atoms, such as sulfamoyl, methylsulfamoyl, dimethylsulfamoyl or phenylsulfamoyl), a carbamoyl group (having preferably from 1 to 30 carbon atoms, more preferably from 1 to 20 carbon atoms, and particularly preferably from 1 to 12 carbon atoms, such as carbamoyl, methylcarbamoyl, diethylcarbamoyl or phenylcarbamoyl), an alkylthio group (having preferably from 1 to 30 carbon atoms, more preferably from 1 to 20 carbon atoms, and particularly preferably from 1 to 12 carbon atoms, such as methylthio or ethylthio), an arylthio group (having preferably from 6 to 30 carbon atoms, more preferably from 6 to 20 carbon atoms, and particularly preferably from 6 to 12 carbon atoms, such as phenylthio), a heteroarylthio group (having preferably from 1 to 30 carbon atoms, more preferably from 1 to 20 carbon atoms, and particularly preferably from 1 to 12 carbon atoms, such as pyridylthio, 2-benzimidazolylthio, 2-benzoxazolylthio or 2-benzthiazolylthio), a sulfonyl group (having preferably from 1 to 30 carbon atoms, more preferably from 1 to 20 carbon atoms, and particularly preferably from 1 to 12 carbon atoms, such as mesyl or tosyl), a sulfinyl group (having preferably from 1 to 30 carbon atoms, more preferably from 1 to 20 carbon atoms, and particularly preferably from 1 to 12 carbon atoms, such as methanesulfinyl or benzenesulfinyl), a ureido group (having preferably from 1 to 30 carbon atoms, more preferably from 1 to 20 carbon atoms, and particularly preferably from 1 to 12 carbon atoms, such as ureido, methylureido or phenylureido), a phosphoric acid amide group (having preferably from 1 to 30 carbon atoms, more preferably from 1 to 20 carbon atoms, and particularly preferably from 1 to 12 carbon atoms, such as diethylphosphoric acid amide or phenylphosphoric acid amide), a hydroxyl group, a mercapto group, a halogen atom (such as fluorine, chlorine, bromine or iodine), a cyano group, a sulfo group, a carboxyl group, a nitro group, a hydroxamic acid group, a sulfino group, a hydrazino group, an imino group, a heterocyclic group (having preferably from 1 to 30 carbon atoms, and more preferably from 1 to 12 carbon atoms, having a heteroatom such as nitrogen, oxygen or sulfur, and specifically including imidazolyl, pyridyl, quinolyl, furyl, thienyl, piperidyl, morpholino, benzoxazolyl, benzimidazolyl or benzthiazolyl), and a silyl group (having preferably from 3 to 40 carbon atoms, more preferably from 3 to 30 carbon atoms, and particularly preferably from 3 to 24 carbon atoms, such as trimethylsilyl or triphenylsilyl). These substituents may be further substituted.

$n^1$, $n^2$ and $n^3$ each represents an integer of from 0 to 4. $n^1$, $n^2$ and $n^3$ are each preferably from 0 to 2, more preferably 0 or 1, and still more preferably 0.

The compound of the invention may be either a so-called low-molecular weight compound having one repeating unit of formula (1), or a so-called oligomer compound or polymer compound having two or more repeating units of formula (1) (the weight average molecular weight (converted to polystyrene) is preferably from 1,000 to 5,000,000, more preferably from 2,000 to 1,000,000, and still more preferably from 3,000 to 100,000). In the case of the polymer compound, the structure represented by formula (1) may be contained either in a main chain of the polymer, or in a side chain thereof. Further, the polymer compound may be either a homopolymer compound, or a copolymer compound. The compound of the invention is preferably the low-molecular weight compound.

Specific examples of the compounds of the invention represented by formula (1), (2) or (3) (hereinafter also referred to as the compounds of the invention) are shown below, but it is to be understood that the invention is not limited thereto.

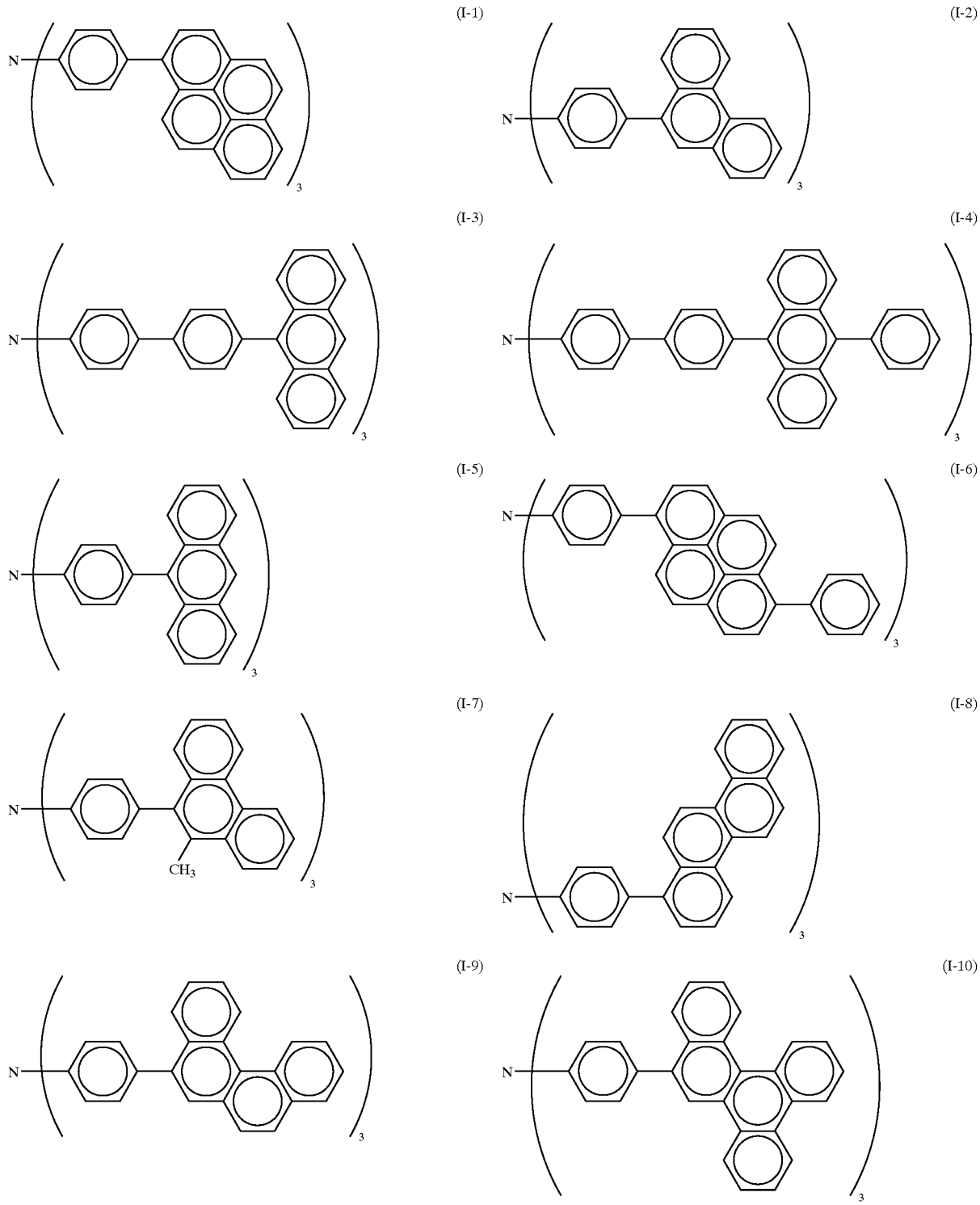

-continued
(I-11) 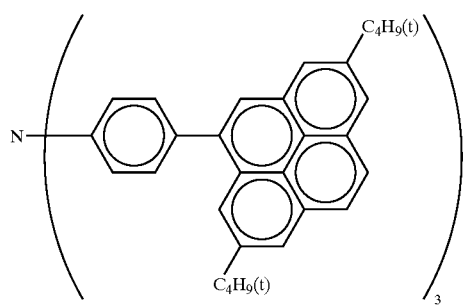
(I-12) 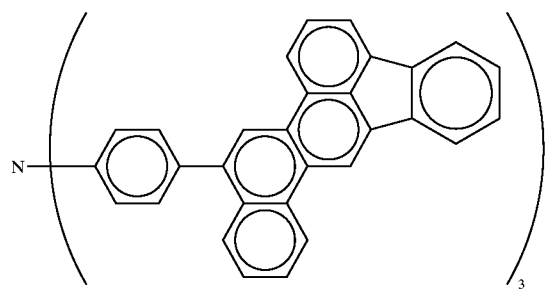
(I-13) 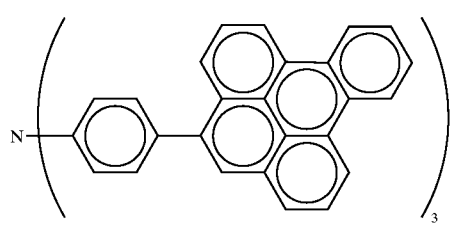
(I-14) 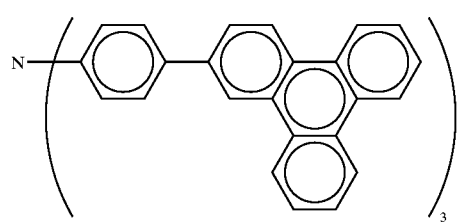
(I-15) 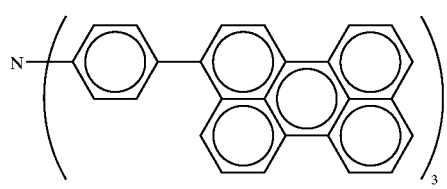
(I-16) 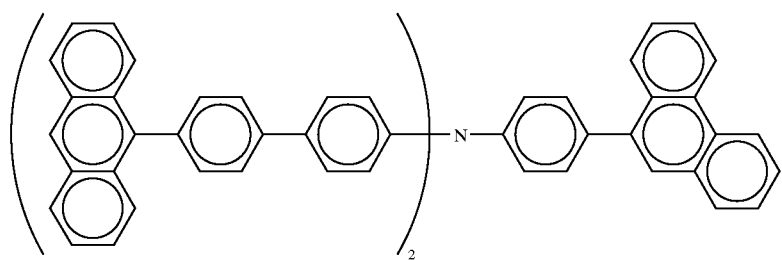
(I-17) 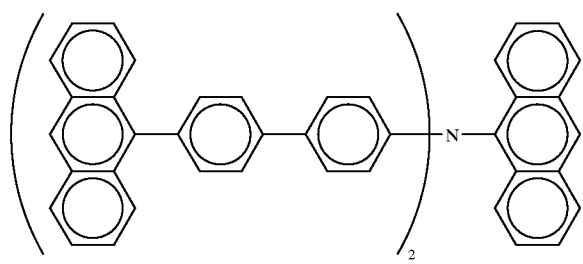
(I-18) 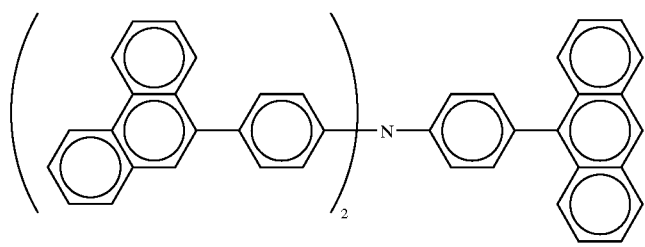

(I-19)
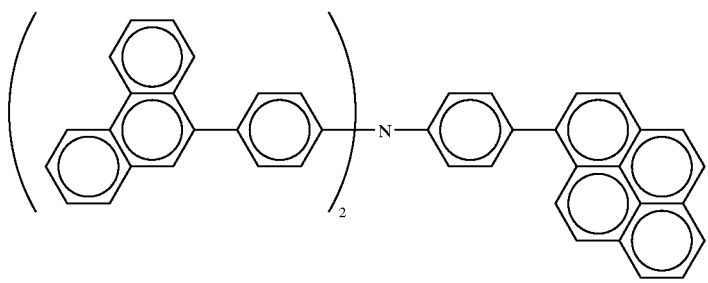
(I-20)
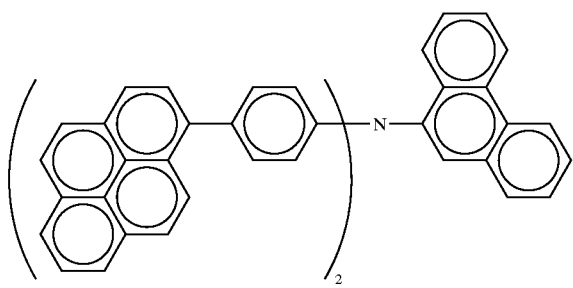
(I-21)
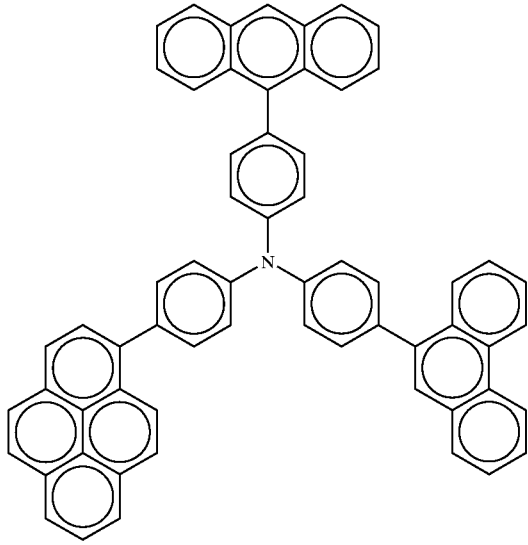
(I-22)
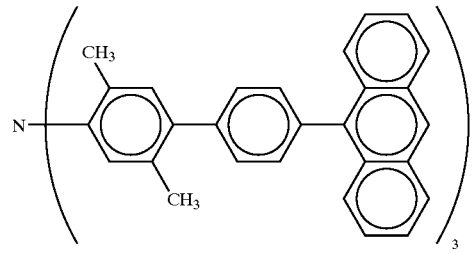
(I-23)
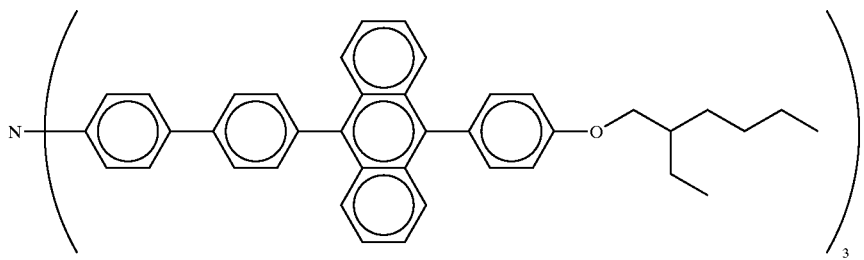
(I-24)
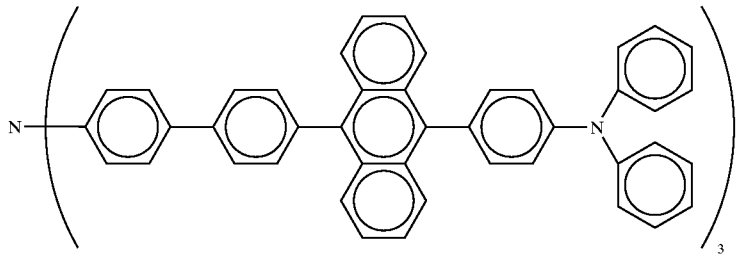

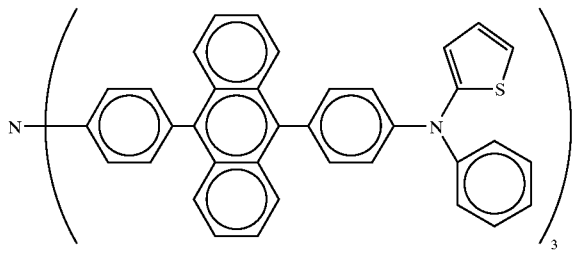
(I-25)

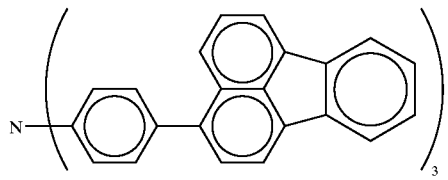
(I-26)

Then, methods for producing the compounds of the invention will be described below. The compounds of the invention can be synthesized by utilizing various known aromatic carbon—carbon bond formation reactions, for example, methods described in *Organic Synthesis Reaction Guide*, pages 617 to 643 (John Wiley & Sons, Inc.) and *Comprehensive Organic Transformation*, pages 5 to 103 (VHC Co.). Specifically, synthesis methods of forming carbon—carbon bonds in the presence of palladium catalysts are preferred, and methods of synthesizing boric acid derivatives and aryl halide derivatives in the presence of palladium catalysts are more preferred.

The boric acid derivatives include substituted or unsubstituted arylboric acid derivatives (for example, 1,4-phenyldiboric acid and 4,4'-biphenyldiboric acid) and heteroarylboric acid derivatives (for example, pyridyldiboric acid).

The halogen atoms of the aryl halide derivatives are preferably chlorine, bromine and iodine, more preferably bromine and iodine, and particularly preferably bromine.

Examples of the palladium catalysts include but are not limited to palladium tetrakis(triphenylphosphine), palladium-carbon, palladium acetate and palladium dichloride (dppf) (dppf: 1,1'-bisdiphenylphosphinoferrocene). Ligands such as triphenylphosphine may be added at the same time.

In this reaction, bases are preferably used. Although there is no particular limitation on the kind of base used, examples thereof include sodium carbonate, sodium acetate and triethylamine. Although there is no particular limitation on the amount of base used, it is preferably from 0.1 to 20 equivalents, and particularly from 1 to 10 equivalents, based on a boric acid (ester) site.

In this reaction, solvents are preferably used. Examples of the solvents used include but are not limited to ethanol, water, ethylene glycol dimethyl ether, diethylene glycol dimethyl ether, dimethylformamide, toluene, tetrahydrofuran and mixed solvents thereof.

The light-emitting devices containing the compounds of the invention will be described below. The light-emitting devices of the invention can be used irrespective of the system, the driving system and the utilizing form, as long as they utilize the compounds of the invention. However, ones utilizing luminescence from the compounds of the invention or utilizing the compounds as charge-transporting materials are preferred. Typical examples of the light-emitting devices include organic EL (electroluminescence) devices.

There is no particular limitation on the method for forming an organic layer of the light-emitting device containing the compound of the invention. Methods such as resistance heating vapor deposition, electron beam processing, sputtering, molecular lamination, coating and ink jet processing are used. In terms of their properties and production, resistance heating vapor deposition and coating are preferred.

The light-emitting device of the invention is an device in which a light-emitting layer or a plurality of organic compound films including a light-emitting layer are formed between a pair of electrodes, an anode and a cathode, and may have a hole-injecting layer, a hole-transporting layer, an electron-injecting layer, an electron-transporting layer and/or a protective layer, in addition to the light-emitting layer. Each of these layers may have another function. Various materials can be used for the formation of the respective layers.

The anodes supply holes to the hole-injecting layers, the hole-transporting layers and the light-emitting layers, and can be formed of metals, alloys, metal oxides, conductive compounds or mixtures thereof, preferably materials having a work function of 4 eV or more. Specific examples thereof include conductive metal oxides such as tin oxide, zinc oxide, indium oxide and indium tin oxide (ITO), metals such as gold, silver, chromium and nickel, further mixtures or laminates of the metals with the conductive metal oxides, inorganic conductive materials such as copper iodide and copper sulfide, organic conductive materials such as polyaniline, polythiophene and polypyrrole, and laminates thereof with ITO. Preferred are conductive metal oxides, and ITO is particularly preferred in terms of productivity, high conductivity and transparency. The thickness of the anode is usually preferably from 10 nm to 5 μm, more preferably from 50 nm to 1 μm, and still more preferably from 100 nm to 500 nm, although it can be appropriately selected depending on the kind of material.

As the anode, there is usually used one in which layer formation is carried out on soda-lime glass, non-alkali glass or a transparent resin substrate. When glass is used, non-alkali glass is preferably used for decreasing ions eluted from glass. When soda lime-glass is used, it is preferable to use one provided with a barrier coat of silica or the like. There is no particular limitation on the thickness of the substrate, as long as it is sufficient to keep its mechanical strength. When glass is used, the thickness is usually 0.2 mm or more, and preferably 0.7 mm or more.

Various methods are used for the preparation of the anodes depending on the kind of material. For example, in the case of ITO, film formation is carried out by methods such as electron beam processing, sputtering, resistance heating vapor deposition, chemical reaction (sol-gel processing) and coating of a dispersion of ITO.

The anodes are also capable of decreasing the driving voltage of the devices and increasing the light-emission efficiency by washing or other treatment. For example, in the case of ITO, UV-ozone treatment and plasma treatment are effective.

The cathodes supply electrons to the electron-injecting layers, the electron-transporting layers and the light-emitting layers, and are selected considering adhesion to layers adjacent to the negative electrodes, such as the electron-injecting layers, the electron-transporting layers and the light-emitting layers, ionization potential and stability. As materials for the cathodes, there can be used metals, alloys, metal halides, metal oxides, conductive compounds or mixtures thereof. Specific examples thereof include alkali metals (for example, Li, Na and K) or fluorides thereof, alkali earth metals (for example, Mg and Ca) or fluorides thereof, gold, silver, lead, aluminum, sodium-potassium alloys or mixed metals thereof, lithium-aluminum alloys or mixed metals thereof, magnesium-silver alloys or mixed metals thereof, and rare earth metals such as indium and ytterbium. Preferred are materials having a work function of 4 eV or less, and more preferred are aluminum, lithium-aluminum alloys or mixed metals thereof and magnesium-silver alloys or mixed metals thereof. The cathode may have not only a single-layer structure of the above-mentioned compound or mixture, but also a laminated structure containing the above-mentioned compound or mixture. The thickness of the cathode is usually preferably from 10 nm to 5 µm, more preferably from 50 nm to 1 µm, and still more preferably from 100 nm to 1 µm, although it can be appropriately selected depending on the kind of material.

For the preparation of the cathodes, methods such as electron beam processing, sputtering, resistance heating vapor deposition and coating are used. The metals can be vapor deposited as simple substances, or two or more components can be vapor deposited at the same time. Further, it is also possible to vapor deposit the plurality of metals at the same time to form an alloy electrode, or an alloy previously prepared may also be vapor deposited.

It is preferred that the sheet resistance of the anodes and the cathodes is so low as several hundred Ω/square or less.

Materials for the light-emitting layers may be any, as long as they can form layers having the function of being able to inject holes from the anodes, the hole-injecting layers or the hole-transporting layers and to inject electrons from the cathodes, the electron-injecting layers or the electron-transporting layers, upon electric field application, the function of transporting injected charges, or the function of providing the field of recombination of holes with electrons to emit light. Examples of the compounds used in the light-emitting layers include benzoxazole derivatives, benzimidazole derivatives, benzthiazole derivatives, styrylbenzene derivatives, polyphenyl derivatives, diphenylbutadiene derivatives, tetraphenylbutadiene derivatives, naphthalimide derivatives, coumarin derivatives, perylene derivatives, perynone derivatives, oxadiazole derivatives, aldazine derivatives, pyralizine derivatives, cyclopentadiene derivatives, bis(styryl)anthracene derivatives, quinacridone derivatives, pyrrolopyridine derivatives, thiadiazolepyridine derivatives, cyclo-pentadiene derivatives, styrylamine derivatives, aromatic dimethylidyne compounds, various metal complexes represented by metal complexes of 8-quinolinol derivatives and rare earth complexes, and polymeric compounds such as polythiophene, polyphenylene and polyphenylenevinylene, organic silane derivatives and the compounds of the invention. Although there is no particular limitation on the thickness of the light-emitting layer, it is usually preferably from 1 nm to 5 µm, more preferably from 5 nm to 1 µm, and still more preferably from 10 nm to 500 nm.

There is no particular limitation on the method for forming the light-emitting layer. Methods such as resistance heating vapor deposition, electron beam processing, sputtering, molecular lamination, coating (spin coating, casting and dip coating), ink jet processing and LB processing are used. Preferred are resistance heating vapor deposition and coating.

Materials for the hole-injecting layers and the hole-transporting layers may be any, as long as they have any of the function of injecting holes from the anodes, the function of transporting holes and the function of blocking electrons injected from the cathodes. Specific examples thereof include carbazole derivatives, triazole derivatives, oxazole derivatives, oxadiazole derivatives, imidazole derivatives, polyarylalkane derivatives, pyrazoline derivatives, pyrazolone derivatives, phenylenediamine derivatives, arylamine derivatives, amino-substituted chalcone derivatives, styrylanthracene derivatives, fluorenone derivatives, hydrazone derivatives, stilbene derivatives, silazane derivatives, aromatic tertiary amine compounds, styrylamine compounds, aromatic dimethylidyne compounds, porphyrin compounds, polysilane compounds, poly(N-vinylcarbazole) derivatives, aniline copolymers, conductive high molecular oligomers such as thiophene oligomers and polythiophene, organic silane derivatives and the compounds of the invention. Although there is no particular limitation of the thickness of the hole-injecting layer and the hole-transporting layer, it is usually preferably from 1 nm to 5 µm, more preferably from 5 nm to 1 µm, and still more preferably from 10 nm to 500 nm. The hole-injecting layer and the hole-transporting layer may have either a single-layer structure comprising one kind or two or more kinds of the above-mentioned materials, or a multilayer structure having a plurality of layers each comprising the same composition or different compositions.

As methods for forming the hole-injecting layers and the hole-transporting layers, there are used vacuum vapor deposition, LB processing, coating (spin coating, casting and dip coating) of the above-mentioned hole-injecting and hole-transporting materials dissolved or dispersed in solvents, and ink jet processing. In the case of coating, the materials can be dissolved or dispersed together with resin components. The resin components include, for example, polyvinyl chloride, polycarbonates, polystyrene, polymethyl methacrylate, polybutyl methacrylate, polyesters, polysulfones, polyphenylene oxide, polybutadiene, poly(N-vinylcarbazole), hydrocarbon resins, ketone resins, phenoxy resins, polyamides, ethyl cellulose, vinyl acetate, ABS resins, polyurethane, melamine resins, unsaturated polyester resins, alkyd resins, epoxy resins and silicone resins.

Materials for the electron-injecting layers and the electron-transporting layers may be any, as long as they have any of the function of injecting electrons from the cathodes, the function of transporting electrons and the function of blocking holes injected from the anodes. Specific examples thereof include triazole derivatives, oxazole derivatives, oxadiazole derivatives, fluorenone derivatives, anthraquinodimethane derivatives, anthrone derivatives, diphenylquinone derivatives, thiopyran dioxide derivatives, carbodiimide derivatives, fluorenylidenemethane derivatives, distyrylpyrazine derivatives, heterocyclic tetra-carboxylic anhydrides such as naphthaleneperylene, phthalocyanine derivatives, various metal complexes represented by metal complexes of 8-quinolinol derivatives, metallophthalocyanine and metal complexes each having benzoxazole or benzothiazole as a ligand, and organic silane derivatives. Although there is no particular limitation of the thickness of the electron-injecting layer and the electron-transporting layer, it is usually preferably from 1 nm to 5 µm, more preferably from 5 nm to 1 µm, and still more preferably from 10 nm to 500 nm. The electron-injecting layer and the electron-transporting layer may have either a single-layer structure comprising one kind or two or more kinds of the above-mentioned materials, or a multilayer structure having a plurality of layers each comprising the same composition or different compositions.

As methods for forming the electron-injecting layers and the electron-transporting layers, there are used vacuum vapor deposition, LB processing and coating (spin coating, casting and dip coating) of the above-mentioned hole-injecting and hole-transporting materials dissolved or dispersed in solvents, and ink jet processing. In the case of coating, the materials can be dissolved or dispersed together with resin components. As the resin components, for example, ones illustrated in the case of the hole-injecting layers and the hole-transporting layers can be applied.

Materials for the protective layers may be any, as long as they have the function of inhibiting promoters of device deterioration such as water and oxygen from entering the devices. Specific examples thereof include metals such as In, Sn, Pb, Au, Cu, Ag, Al, Ti and Ni, metal oxides such as MgO, SiO, $SiO_2$, $Al_2O_3$, GeO, NiO, CaO, BaO, $Fe_2O_3$, $Y_2O_3$ and $TiO_2$, metal fluorides such as $MgF_2$, LiF, $AlF_3$ and $CaF_2$, polyethylene, polypropylene, polymethyl methacrylate, polyimides, polyureas, polytetrafluoroethylene, polychlorotrifluoroethylene, polydichlorodifluoroethylene, co-polymers of chlorotrifluoroethylene and dichlorodifluoroethylene, copolymers obtained by copolymerizing monomer mixtures each containing tetrafluoroethylene and at least one kind of comonomer, fluorine-containing copolymers having cyclic structures on main chains of the copolymers, water-absorptive substances having a water absorption of 1% or more, and moisture-proof substances having a water absorption of 0.1% or less.

There is no particular limitation on the method for forming the protective layer. For example, vacuum vapor deposition, sputtering, reactive sputtering, MBE (molecular beam epitaxy) processing, cluster ion beam processing, ion plating, plasma polymerization (high-frequency excitation ion plating), plasma CVD, laser CVD, thermal CVD, gas source CVD and coating can be applied.

The invention will be further illustrated in detail below with reference to the following examples, which are, however, not to be construed as limiting the invention.

Synthesis of Compound (1-1)

Diethylene glycol dimethyl ether (50 ml) and 50 ml of water were added to 1.5 g of pyreneboric acid ester a, 0.67 g of tris(p-bromophenyl)benzene, 1.47 g of sodium carbonate, 0.05 g of triphenylphosphine and 0.05 g of palladium-carbon, followed by stirring under reflux. After 6 hours, the reaction solution was diluted with 200 ml of chloroform and 200 ml of water, and filtered through cerite. The organic layer was washed with two 100 ml portions of water, and dried on sodium sulfate, followed by concentration of solvent. After purification by column chromatography (chloroform), purification was conducted by recrystallization (chloroform/methanol) to obtain 0.8 g of compound (1-1). A vapor-deposited film of compound (1-1) was prepared, and the film fluorescence thereof was measured. As a result, the maximum wavelength (max) of the film fluorescence was 473 nm.

Synthesis of Compound (1-2)

Diethylene glycol dimethyl ether (50 ml) and 50 ml of water were added to 1.0 g of boric acid ester b, 0.38 g of tris(p-bromophenyl)benzene, 0.85 g of sodium carbonate, 0.05 g of triphenylphosphine and 0.05 g of palladium-carbon, followed by stirring under reflux. After 6 hours, the reaction solution was diluted with 200 ml of chloroform and 200 ml of water, and filtered through cerite. The organic layer was washed with two 100 ml portions of water, and dried on sodium sulfate, followed by concentration of solvent. After purification by column chromatography (chloroform), purification was conducted by recrystallization (chloroform/methanol) to obtain 0.4 g of white solid compound (1-2).

Synthesis of Compound (1-3)

Diethylene glycol dimethyl ether (50 ml) and 50 ml of water were added to 1.5 g of boric acid ester c, 0.72 g of tris(p-bromophenyl)benzene, 1.6 g of sodium carbonate, 0.05 g of triphenylphosphine and 0.05 g of palladium-carbon, followed by stirring under reflux. After 6 hours, the reaction solution was diluted with 200 ml of chloroform and 200 ml of water, and filtered through cerite. The organic layer was washed with two 100 ml portions of water, and dried on sodium sulfate, followed by concentration of solvent. After purification by column chromatography (chloroform), purification was conducted by recrystallization (chloroform/methanol) to obtain 0.9 g of compound (1-3). The glass transition point (Tg) measured by differential scanning calorimetry (DSC) was 153° C.

Reaction schemes of the above-mentioned compounds (1-1), (1-2) and (1-3) of the invention are shown below.

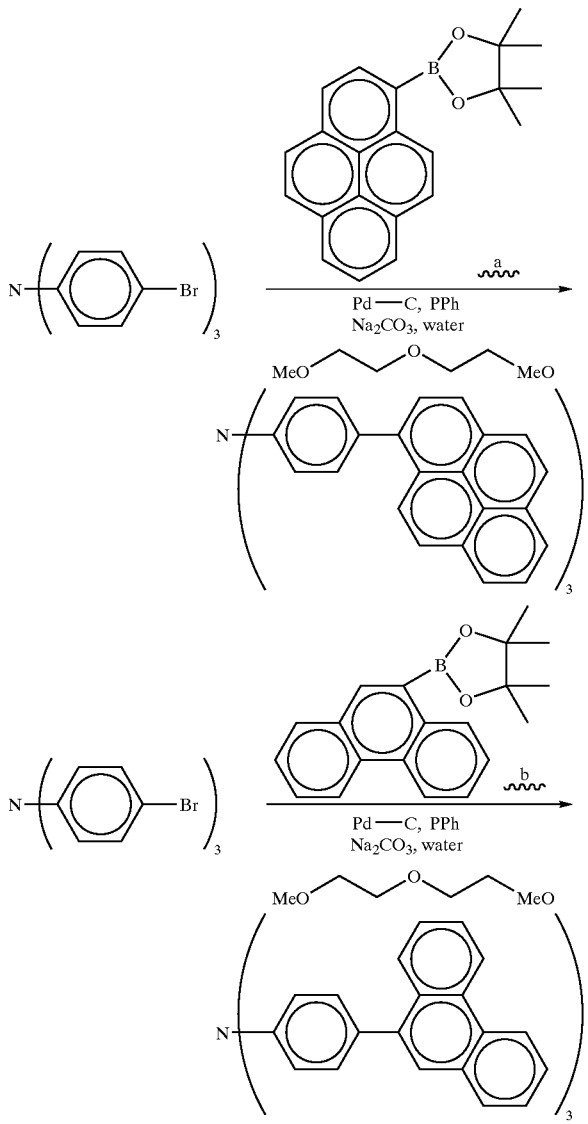

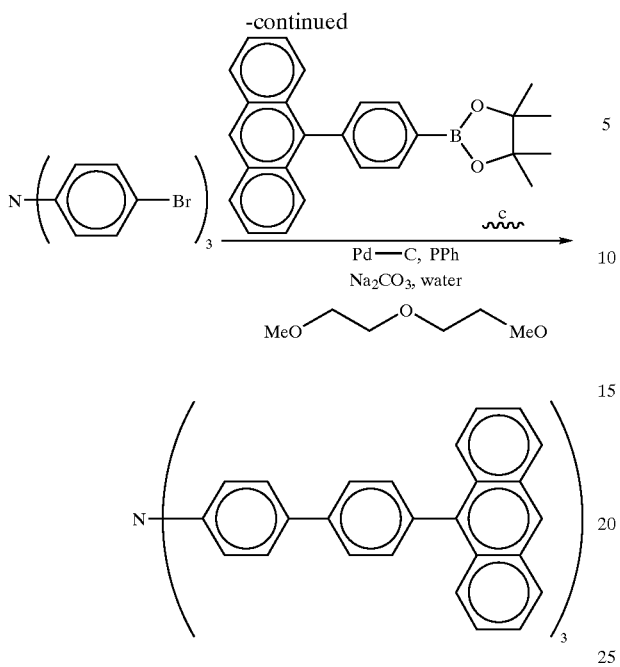

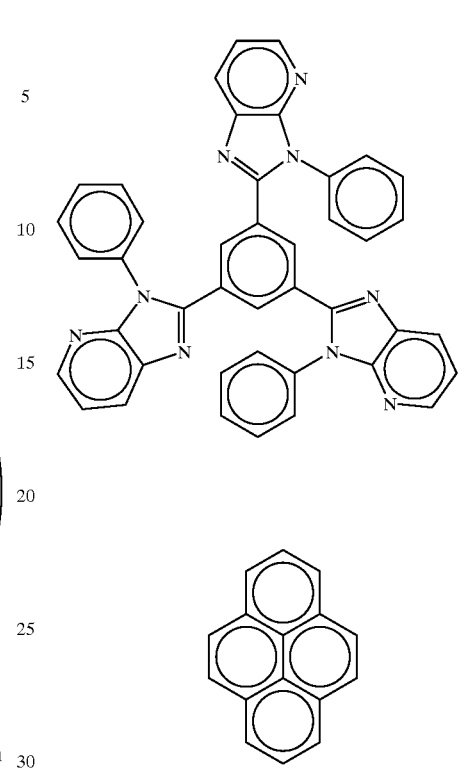

Compound B

Compound C

Compound D

COMPARATIVE EXAMPLE 1

A washed ITO substrate was placed in a vapor deposition apparatus, and vapor deposited with α-NPD (N,N'-diphenyl-N,N'-di (α-naphthyl)-benzidine) to a thickness of 40 nm. Then, distyryl compound A was vapor deposited thereon to a thickness of 20 nm, and azole compound B was vapor deposited thereon to a thickness of 40 nm, thereby preparing a device. A mask patterned (a mask giving a luminescence area of 4 mm×5 mm) was placed on the organic thin film, and in a vapor deposition apparatus, magnesium/silver of 10/1 were concurrently vapor deposited to a thickness of 50 nm, followed by vapor deposition of silver to a thickness of 50 nm. With Source Measure Unit Model 2400 (manufactured by Toyo Technica K.K.), a direct current constant voltage was applied to the EL device to allow the device to emit light. The luminance thereof was measured with Luminance Meter BM-8 (manufactured by Topcon K.K.), and the emission wavelength was measured with Spectrum Analyzer PMA-11 (manufactured by Hamamatsu Photonics K.K.) As a result, blue-green luminescence having a CIE chromaticity value of (x, y)=(0.15, 0.20) and the luminance having a maximum luminance of 1130 cd/m$^2$ were obtained. When the device was allowed to stand for one day in an atmosphere of nitrogen, it was observed that a surface of the organic thin film became clouded.

Compound A

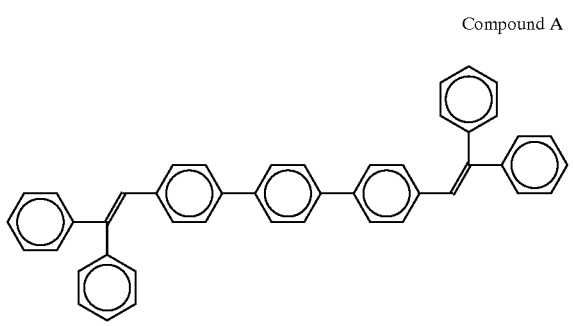

COMPARATIVE EXAMPLE 2

A device was prepared in the same manner as with Comparative Example 1 with the exception that compound C was used in place of compound A used in Comparative Example 1. An organic thin film became clouded, and the evaluation of the device was impossible.

COMPARATIVE EXAMPLE 3

A device was prepared in the same manner as with Comparative Example 1 with the exception that compound D was used in place of compound A used in Comparative Example 1. When the device was allowed to stand for one day in an atmosphere of nitrogen, it was observed that a surface of an organic thin film became clouded.

EXAMPLE 1

A device was prepared in the same manner as with Comparative Example 1 with the exception that compound (1-1) of the invention was used in place of compound A used in Comparative Example 1. The device was evaluated in the same manner as with Comparative Example 1. As a result, blue-green luminescence of (0.19, 0.29) and a maximum luminance of 4280 cd/m² were obtained. Even when the device was allowed to stand for one day in an atmosphere of nitrogen, an organic film was transparent.

EXAMPLE 2

A washed ITO substrate was placed in a vapor deposition apparatus, and vapor deposited with α-NPD (N,N'-diphenyl-N,N'-di (α-naphthyl)-benzidine) to a thickness of 40 nm. Then, distyryl compound A and compound (1-1) of the invention (distyryl compound A: compound (1-1)=50:1) were concurrently vapor deposited thereon to a thickness of 20 nm, azole compound B was vapor deposited thereon to a thickness of 40 nm, and a cathode was vapor deposited in the same manner as with Comparative Example 1, thereby preparing a device. The device was evaluated in the same manner as with Comparative Example 1. As a result, blue luminescence of (0.16, 0.15) and a maximum luminance of 9600 cd/m² were obtained. Even when the device was allowed to stand for one day in an atmosphere of nitrogen, an organic film was transparent.

EXAMPLE 3

Polyvinylcarbazole (40 mg), 12 mg of PBD (p-t-butyl-phenyl-biphenyl-1,2,4-oxadiazole) and 1 mg of compound (1-1) of the invention were dissolved in 3 ml of dichloroethane, and the resulting solution was applied onto a washed substrate by spin coating (2000 rpm, 5 seconds). A cathode was vapor deposited in the same manner as with Comparative Example 1, thereby preparing a device. The device was evaluated in the same manner as with Comparative Example 1. As a result, blue luminescence of (0.15, 0.15) and a maximum luminance of 3180 cd/m² were obtained.

EXAMPLE 4

A device was prepared in the same manner as with Comparative Example 1 with the exception that compound (1-2) of the invention and compound (1-1) of the invention were used in place of NPD and compound A, respectively, used in Comparative Example 1. The device was evaluated in the same manner as with Comparative Example 1. As a result, blue-green luminescence of (0.19, 0.27) and a maximum luminance of 4990 cd/m² were obtained. Even when the device was allowed to stand for one day in an atmosphere of nitrogen, an organic film was transparent. Further, the device was heated at 100° C. for one hour in an atmosphere of nitrogen. However, no increase in dark spots was observed. On the other hand, for the device of Example 1, an increase in dark spots was observed under the same conditions.

Similarly, EL devices containing the compounds of the invention were prepared and evaluated. As a result, it was confirmed that the compounds of the invention had high functions (luminance, durability and film forming properties) as EL device materials.

The compounds of the invention are usable as the organic EL device materials, and also applicable to medical purposes, fluorescent brightening agents, photographic materials, UV absorbing materials, laser dyes, dyes for color filters and color converting filters.

While the invention has been described in detail and with reference to specific embodiments thereof, it will be apparent to one skilled in the art that various changes and modifications can be made therein without departing from the spirit and scope thereof.

What is claimed is:

1. An organic light-emitting device comprising a light-emitting layer or a plurality of organic compound thin layers including a light-emitting layer formed between a pair of electrodes, wherein at least one layer comprises at least one compound represented by the following formula (2):

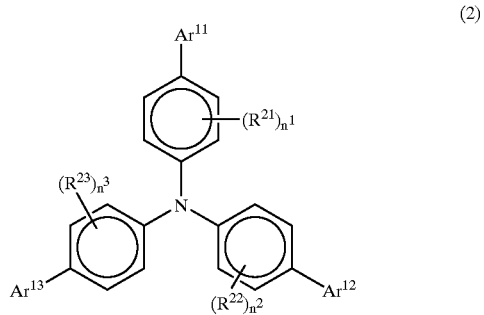

(2)

wherein $Ar^{11}$, $Ar^{12}$ and $Ar^{13}$ each represents a phenanthryl group, a pyrenyl group, a perylenyl group, a chrysenyl group, a fluoranthenyl group, a triphenylenyl group or groups in which cyclocondensation is further conducted to these structures, $R^{21}$, $R^{22}$ and $R^{23}$ each represents a substituent, and $n^1$, $n^2$ and $n^3$ each represents an integer of from 0 to 4.

2. The organic light-emitting device according to claim 1, wherein $Ar^{11}$, $Ar^{12}$ and $Ar^{13}$ each represents a phenanthryl group, a fluoranthenyl group or a pyrenyl group.

3. The organic light-emitting device according to claim 1, wherein the compound represented by the formula (2) is utilized as a charge-transporting material.

4. The organic light-emitting device according to claim 1, wherein the layer comprising the compound represented by the formula (2) is formed by a coating method.

5. A compound represented by the following formula (2):

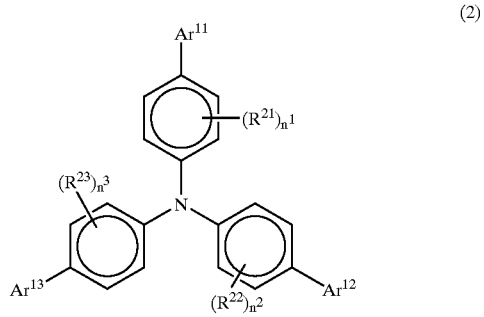

(2)

wherein $Ar^{11}$, $Ar^{12}$ and $Ar^{13}$ each represents a phenanthryl group, a pyrenyl group, a perylenyl group, a chrysenyl group, a fluoranthenyl group, a triphenylenyl group or groups in which cyclocondensation is further conducted to these structures, $R^{21}$, $R^{22}$ and $R^{23}$ each represents a substituent, and $n^1$, $n^2$ and $n^3$ each represents an integer of from 0 to 4.

6. The compound according to claim 5, wherein $A^{11}$, $Ar^{12}$ and $Ar^{13}$ each represents a phenanthryl group, a fluoranthenyl group or a pyrenyl group.

7. An organic light-emitting device comprising a light-emitting layer or a plurality of organic compound thin layers including a light-emitting layer formed between a pair of electrodes, wherein at least one layer comprises at least one compound represented by the following formula (1):

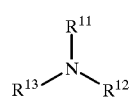
(1)

wherein $R^{11}$, $R^{12}$ and $R^{13}$ each represents a substituted or unsubstituted phenanthryl group, a substituted or unsubstituted fluoranthenyl group, or a substituted or unsubstituted phenanthrylphenyl group.

8. The organic light-emitting device according to claim 7, wherein $R^{11}$, $R^{12}$ and $R^{13}$ each represents a substituted or unsubstituted phenanthryl group or a substituted or unsubstituted phenanthrylphenyl group.

9. The organic light-emitting device according to claim 8, wherein $R^{11}$, $R^{12}$ and $R^{13}$ each represents an alkyl-substituted group.

10. The organic light-emitting device according to claim 7, wherein a substituent for $R^{11}$, $R^{12}$ and $R^{13}$ is an alkyl group.

11. The organic light-emitting device according to claim 7, wherein the compound represented by the formula (1) is utilized as a charge-transporting material.

12. The organic light-emitting device according to claim 7, wherein the layer comprising the compound represented by the formula (1) is formed by a coating method.

13. The organic light-emitting device according to claim 7, wherein $R^{11}$, $R^{12}$ and $R^{13}$ each represents a substituted or unsubstituted fluoranthenyl group.

14. The organic light-emitting device according to claim 13, wherein $R^{11}$, $R^{12}$ and $R^{13}$ each represents an alkyl-substituted group.

* * * * *